United States Patent [19]

Los

[11] 4,221,586

[45] * Sep. 9, 1980

[54] IMIDAZOLINYL BENZAMIDES AS HERBICIDAL AGENTS

[75] Inventor: Marinus Los, Pennington, N.J.

[73] Assignee: American Cyanamid Company, Stamford, Conn.

[*] Notice: The portion of the term of this patent subsequent to Oct. 23, 1995, has been disclaimed.

[21] Appl. No.: 7,739

[22] Filed: Jan. 30, 1979

[51] Int. Cl.$^2$ .............................................. A01N 9/22
[52] U.S. Cl. ......................................................... 71/92
[58] Field of Search ............................................ 71/92

[56] References Cited

U.S. PATENT DOCUMENTS

| 2,472,347 | 6/1949 | Sexton | 71/118 |
| 2,949,354 | 8/1960 | Todd | 71/118 |
| 3,947,263 | 3/1976 | Brouwer et al. | 71/92 |
| 3,964,896 | 6/1976 | Brouwer et al. | 71/92 |
| 4,055,409 | 10/1977 | Johnson et al. | 71/92 |
| 4,122,275 | 10/1978 | Los | 71/92 |

Primary Examiner—Glennon H. Hollrah
Attorney, Agent, or Firm—H. G. Jackson

[57] ABSTRACT

The invention is a method for the control of undesirable plant species by the application of a herbicidally effective amount of an imidazolinyl benzamide to the foliage of the undesirable plants or to soil containing seeds or other propagating organs of the plants.

9 Claims, No Drawings

IMIDAZOLINYL BENZAMIDES AS HERBICIDAL AGENTS

DESCRIPTION OF THE INVENTION

The invention is the use as herbicidal agents of imidazolinyl benzamides having the structure:

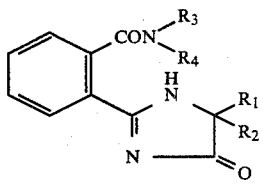

wherein $R_1$ is alkyl $C_1$–$C_4$; $R_2$ is alkyl $C_1$–$C_6$, cycloalkyl $C_3$–$C_6$, alkenyl $C_2$–$C_4$, phenyl, halophenyl or benzyl; and when $R_1$ and $R_2$ are taken together with the carbon to which they are attached they may form cycloalkyl $C_3$–$C_6$ optionally substituted with methyl; $R_3$ and $R_4$ each individually represent hydrogen, alkyl $C_1$–$C_4$, alkenyl $C_3$–$C_5$, alkynyl $C_3$–$C_5$, or benzyl; and when $R_1$ and $R_2$ represent different substituents, the optical isomers thereof.

While the imidazolinyl benzamides of this invention are illustrated by the structure identified as formula (I) above, it should be understood that these compounds may be tautomeric. As such, they could have the structure:

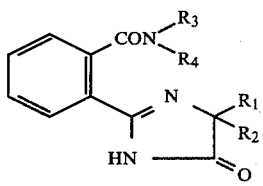

wherein $R_1$, $R_2$, $R_3$ and $R_4$ are as described. Both tautomeric forms are, of course, intended to be included as compounds of the invention when reference is made throughout the specification and claims to the formula I structure.

In accordance with the invention, imidazolinyl benzamides claimed in my U.S. Pat. No. 4,122,275 (1978) having the structure:

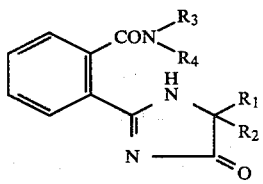

wherein $R_1$, $R_2$, $R_3$ and $R_4$ are as described above, can be prepared by reacting an imidazoisoindoledione having the structure:

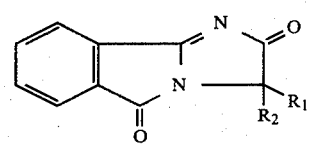

where $R_1$ and $R_2$ are as described above, with an amine represented by the formula: $R_4R_3NH$ (III) where $R_3$ and $R_4$ are as described above.

The mole ratio of amine (III) to imidazoisoindoledione (II) should be in the range of 1:1 to 10:1, and preferably 2:1 to 5:1. The reaction is preferably conducted in a non-protic solvent such as tetrahydrofuran, dioxane, toluene, xylene, benzene, or the like, at a temperature between 5° C. and 100° C.

It should also be understood that when $R_1$ and $R_2$ represent different substituents, the carbon to which $R_1$ and $R_2$ are attached is an asymmetric center and the products (as well as their intermediates) exist in d- and l- forms as well as dl- forms. Further, when the imidazoisoindoledione (II) is optically active and either the d- or l- isomer is reacted with the formuala (III) amine, $R_4R_3NH$, the corresponding d- or l-imidazolinyl benzamide (I) is formed.

The intermediate imidazoisoindoledione (II), which are essential to the preparation of the formula (I) imidazolinyl benzamides of the present invention, are described with a method for their preparation in my U.S. Pat. No. 4,017,510 (1977).

The method for the preparation of the compounds of the invention may be graphically illustrated as follows:

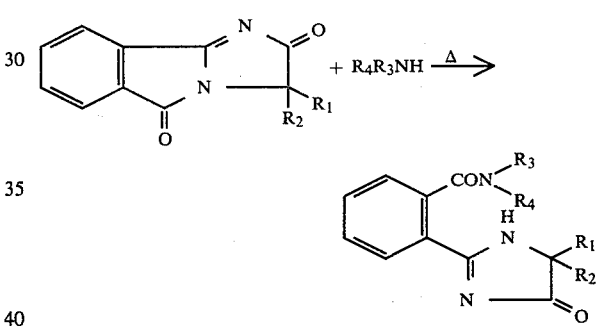

wherein $R_1$, $R_2$, $R_3$ and $R_4$ are as described above.

Illustrative of the compounds useful in the invention are:
o-(5-isopropyl-5-methyl-4-oxo-2-imidazolin-2-yl)-3-butynylbenzamide;
o-(5,5-diethyl-4-oxo-2-imidazolin-2-yl)-N,N-di-ethylbenzamide;
o-(5-isopropyl-5-methyl-4-oxo-2-imidazolin-2-yl)-N-2-butenylbenzamide;
o-(5-isopropyl-5-methyl-4-oxo-2-imidazolin-2-yl)-N-methylbenzamide;
o-(5-isopropyl-5-methyl-4-oxo-2-imidazolin-2-yl)-N-isopropylbenzamide;
o-(5-isopropyl-5-methyl-4-oxo-2-imidazolin-2-yl)-N-allylbenzamide;
o-(5-isopropyl-5-methyl-4-oxo-2-imidazolin-2-yl)-N,N-diallylbenzamide;
o-(5-isopropyl-5-methyl-4-oxo-2-imidazolin-2-yl)-N-1,1-dimethyl-2-propynylbenzamide;
o-(5-n-propyl-5-methyl-4-oxo-2-imidazolin-2-yl)-N-1,1-dimethylallylbenzamide;
o-(5-isopropyl-5-methyl-4-oxo-2-imidazolin-2-yl)-N,N-diphenylbenzamide;
o-(5-cyclohexyl-5-methyl-4-oxo-2-imidazolin-2-yl)-N-2-propynylbenzamide;
o-(5-benzyl-5-methyl-4-oxo-2-imidazolin-2-yl)-N,N-diisopropylbenzamide;

o-(5-isopropyl-5-methyl-4-oxo-2-imidazolin-2-yl)-N-benzylbenzamide; and o-(4-oxo-1,3-diazospiro[4,5]dec-2-en-2-yl)-N-n-propylbenzamide.

Preferred compounds of the invention have the structure of formula I above, wherein $R_1$ is methyl; $R_2$ is alkyl $C_1$-$C_3$, preferably isopropyl, cyclohexyl or benzyl, or when $R_1$ and $R_2$ are taken together with the carbon to which they are attached they may represent cyclohexyl; $R_3$ and $R_4$ each individually represent hydrogen, alkyl $C_1$-$C_3$, allyl, dimethylallyl, propynyl, or benzyl; and when $R_1$ and $R_2$ are different, the optical isomers thereof.

The compounds of this invention, as represented by formula I above, are useful as herbicidal agents. They are effective for the control of undesirable broadleaf weeds (dicotyledonous plants), sedges and grass plants (monocotyledonous plants), and may be used effectively for the control of such plants by application thereof to the foliage of the plants or to soil containing seeds or other propagating organs of the plants.

Postemergence control of undesirable plants, particularly broadleaf plants such as mustard, pigweed and morningglory, can be achieved by applying a herbicidally effective amount of the formula I imidazolinyl benzamide to the foliage of the plants, preferably as a dilute liquid spray.

In practice, generally about 0.28 to 11.2 kg per hectare of the formula I imidazolinyl benzamide will provide postemergence control of the above-identified plants.

Preemergence control of both broadleaf weeds such as mustard, pigweed, morningglory, teaweed and velvetleaf; purple nutsedge, and grass plants such as barnyardgrass, crabgrass and green foxtail, is obtained when the formula I imidazolinyl benzamide is applied in a herbicidally effective amount, preferably also as a dilute liquid spray or as a granular formulation, to soil containing seeds or nutlets of the undesirable plants. Generally about 0.28 kg to 11.2 kg per hectare, and preferably 1.12 kg to 11.2 kg per hectare, will provide the desired control.

Inasmuch as the compounds of this invention are relatively insoluble in water and other common organic solvents, it is generally most advantageous to prepare the formula I imidazolinyl benzamides either as granular formulations or as wettable powders or flowable liquids. These latter formulations are then dispersed in water or other inexpensive organic solvent for application as liquid sprays.

Wettable powders can be prepared by grinding together about 20% to 45% by weight of a finely divided carrier such as attapulgite, bentonite, kaolin, diatomaceous earth, or the like, 45% to 80% by weight of the imidazolinyl benzamide, 2 to 5% by weight of a dispersing agent such as the sodium salt of condensed naphthalene sulfonic acids, sodium lignosulfonate, or the like, and 2% to 5% by weight of a surfactant such as sodium N-methyl-N-oleoyl taurate, alkyl phenoxy polyoxyethylene ethanol, or the like.

A typical flowable liquid can be prepared by admixing about 40% by weight of the formula I benzamide with about 2% by weight of gelling clay, 1% by weight of polyethylene glycol, 3% by weight of the sodium salt of condensed naphthalene sulfonic acids, and 54% by weight of water.

A typical granular formulation can be prepared by dissolving or dispersing the active ingredient in solvent and applying the solution or dispersion to a sorptive or non-sorptive carrier in sufficient amount to provide 10% to 15% by weight of toxicant on the granular carrier.

The invention in the present application is further demonstrated by the examples set forth below.

EXAMPLE 1

Preparation of o-(5-Isopropyl-5-methyl-4-oxo-2-imidazolin-2-yl)-N,N-dimethylbenzamide To a cold solution of 180 g of 3-isopropyl-3-methyl-5H-imidazo[2,1-a]isoindole-2(3H),5-dione in 300 ml of dry tetrahydrofuran in a pressure bottle is added 68 g of dimethylamine. The bottle is sealed and the mixture heated to 50° C. with stirring for 16 hours. The mixture is cooled, and the contents of the bottle transferred to a flask. The solvent is then removed in vacuo. The crystalline residue is then suspended in ether, filtered, washed with ether, and airdried to give 195 g of o-(5-isopropyl-5-methyl-4-oxo-2-imidazolin-2-yl)-N,N-dimethylbenzamide, melting point 144°–146° C. This product is recrystallized from acetonitrile to give an analytically pure product, melting point 147°–150° C.

EXAMPLE 2

Preparation of Formula I Imidazolinyl Benzamides

Using essentially the same procedure as that described in Example 1, but substituting the appropriate imidazo[2,1-a]isoindole-2(3H),5-dione and the appropriate amine for dimethylamine, yields the compounds set forth below.

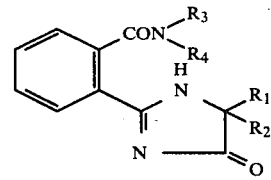

| $R_1$ | $R_2$ | $R_3$ | $R_4$ | Melting Point °C. |
|---|---|---|---|---|
|  | —(CH$_2$)$_5$— | H | H | 211–212 |
| CH$_3$ | CH(CH$_3$)$_2$ | H | H | 174–175 |
| CH$_3$ | CH(CH$_3$)$_2$ | H | CH$_3$ | 203–204 |
|  | —(CH$_2$)$_5$— | CH$_3$ | CH$_3$ | 189–190.5 |
|  | —(CH$_2$)$_5$— | H | CH$_3$ | 259–261 |
| CH$_3$ | CH(CH$_3$)$_2$ | H | —CH$_2$C≡CH | 202–205 |

EXAMPLE 3

The postemergence herbicidal activity of the compounds of the invention is demonstrated by the following tests, wherein a variety of monocotyledonous and dicotyledonous plants and a sedge species are treated with test compounds dispersed in aqueous acetone mixtures. In the tests, seedling plants are grown in individual pots for about 2 weeks, prior to being treated with respective compounds. The test compounds are dispersed in 50/50 acetone/water mixtures containing 0.5% TWEEN® 20, a polyoxyethylene sorbitan monolaurate surfactant of Atlas Chemical Industries, in sufficient quantity to provide the equivalent of about 0.28 kg to 11.2 kg per hectare of active compound when applied to the plants through a spray nozzle operating at 40 psi for a predetermined time. After spraying, the plants are placed on greenhouse benches and are cared for in the usual manner, commensurate with conventional greenhouse practices. Two weeks after treatment, the seedling plants, with the exception of wild oats which are rated at 5 weeks, are examined and rated according to the rating system provided below. The data obtained are reported in Table I below.

| Rating System: | % Difference in Growth from the Check* |
|---|---|

MG—Morningglory (*Ipomoea purpurea*)
BA—Barnyardgrass (*Echinochloa crusgalli*)
CR—Crabgrass (*Digitaria sanguinalis*)
FO—Green Foxtail (*Setaria viridis*)
WO—Wild Oats (*Avena fatus*)
TW—Teaweed (*Sida sponosa*)
VL—Velvetleaf (*Abutilon theophrasti*)
CN—Corn (*Zea mays*)
CO—Cotton (*Gossypium hirsutum*)
SY—Soybean (*Glycine max*)
RI—Rice (*Oryza sativa*)

TABLE I

Postemergence Herbicidal Activity for Compounds having the Structure:

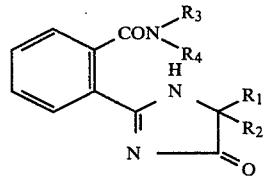

| Structure | | | | Rate kg per | Plant Species | | | | | | | |
|---|---|---|---|---|---|---|---|---|---|---|---|---|
| R₁ | R₂ | R₃ | R₄ | Hectare | PN | SE | MU | PI | RW | MG | TW | VL |
| CH₃ | CH(CH₃)₂ | H | H | 11.2 | 4 | 0 | 6 | 8 | 4 | 4 | 6 | 5 |
| | | | | 4.48 | 2 | 2 | 9 | 9 | 2 | 8 | 5 | 6 |
| | | | | 1.12 | 2 | 0 | 9 | 9 | 0 | 7 | 0 | 2 |
| | | | | 0.56 | 0 | 0 | 9 | 8 | 0 | 7 | 0 | 0 |
| | | | | 0.28 | 0 | 0 | 9 | 8 | 0 | 4 | 0 | 0 |
| CH₃ | CH(CH₃)₂ | CH₃ | CH₃ | 11.2 | 1 | 0 | 8 | 8 | 0 | 4 | 1 | 4 |
| | | | | 4.48 | 5 | 3 | 9 | 9 | 0 | 6 | 2 | 2 |
| | | | | 1.12 | 2 | 0 | 9 | 8 | 0 | 4 | 0 | 0 |
| | | | | 0.56 | 0 | 0 | 9 | 8 | 0 | 4 | 0 | 0 |
| CH₃ | CH(CH₃)₂ | H | —CH₂C≡CH | 11.2 | 0 | 0 | 8 | 3 | 0 | 0 | 5 | 4 |

| Structure | | | | Rate kg per | Plant Species | | | | | | | |
|---|---|---|---|---|---|---|---|---|---|---|---|---|
| R₁ | R₂ | R₃ | R₄ | Hectare | BA | CR | FO | WO | CN | CO | SY | RI |
| CH₃ | CH(CH₃)₂ | H | H | 11.2 | 4 | 4 | 4 | 4 | — | — | — | — |
| | | | | 4.48 | 0 | 0 | 2 | — | 4 | 9 | 9 | 7 |
| | | | | 1.12 | 0 | 0 | 0 | 0 | 0 | 8 | 8 | 0 |
| | | | | 0.56 | 0 | 0 | 0 | 0 | 0 | 7 | 7 | 0 |
| | | | | 0.28 | 0 | 0 | 0 | 0 | 0 | 4 | 4 | 0 |
| CH₃ | CH(CH₃)₂ | CH₃ | CH₃ | 11.2 | 0 | 0 | 0 | 0 | — | — | — | — |
| | | | | 4.48 | 0 | 0 | 2 | — | 7 | 7 | 7 | 0 |
| | | | | 1.12 | 0 | 0 | 0 | — | 6 | 7 | 4 | 0 |
| | | | | 0.56 | 0 | 0 | 0 | — | 2 | 4 | 4 | 0 |
| CH₃ | CH(CH₃)₂ | H | —CH₂C≡CH | 11.2 | 0 | 0 | 0 | 0 | — | — | — | — |

| | |
|---|---|
| 0 - No effect | 0 |
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth, that is, a definite physiological malformation but with an over-all effect less than a 5 on the rating scale. | |

*Based on visual determination of stand, size, vigor, chlorosis, growth malformation and over-all plant appearance.

Plant Abbreviations

PN—Purple Nutsedge (*Cyperus rotundus L.*)
SE—Sesbania (*Sesbania exaltata*)
MU—Mustard (*Brassica kaber*)
PI—Pigweed (*Amaranthus retroflexus*)
RW—Ragweed (*Ambrosia artemisiifolia*)

EXAMPLE 4

The preemergence herbicidal activity of the compounds of the present invention is exemplified by the following tests in which the seeds of a variety of monocotyledonous, dicotyledonous and sedge plants are separately mixed with potting soil and planted on top of approximately 25 mm of soil in separate cups. After planting, the cups are sprayed with the selected aqueous acetone solution containing test compound in sufficient quantity to provide the equivalent of about 0.28 kg to 11.2 kg per hectare of test compound per cup. The treated cups are then placed on greenhouse benches, watered and cared for in accordance with conventional greenhouse procedures. Two to four weeks after treatment, the tests are terminated and each cup is examined and rated according to the rating system set forth above. The herbicidal proficiency of the active ingredients of the present invention is evident from the test results which are reported in Table II below.

TABLE II

Preemergence Herbicidal Activity for Compounds having the Structure:

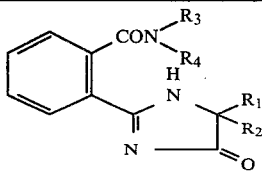

| Structure | | | | Rate kg per | Plant Species | | | | | | | |
|---|---|---|---|---|---|---|---|---|---|---|---|---|
| $R_1$ | $R_2$ | $R_3$ | $R_4$ | Hectare | PN | SE | MU | PI | RW | MG | TW | VL |
| $CH_3$ | $CH(CH_3)_2$ | H | H | 11.2 | 9 | 1 | 8 | 8 | 0 | 8 | 8 | 7 |
| | | | | 4.48 | 9 | 0 | 9 | 9 | 0 | 7 | 0 | 6 |
| | | | | 1.12 | 7 | 0 | 8 | 8 | 0 | 7 | 0 | 2 |
| | | | | 0.56 | 0 | 0 | 6 | 0 | 0 | 5 | 0 | 0 |
| $CH_3$ | $CH(CH_3)_2$ | H | $CH_3$ | 11.2 | 6 | 0 | 8 | 9 | 0 | 4 | 0 | 2 |
| $CH_3$ | $CH(CH_3)_2$ | $CH_3$ | $CH_3$ | 11.2 | 9 | 7 | 9 | 9 | 0 | 8 | 6 | 8 |
| | | | | 4.48 | 9 | 8 | 9 | 9 | 0 | 7 | 1 | 7 |
| | | | | 1.12 | 9 | 1 | 8 | 8 | 0 | 4 | 0 | 1 |
| | | | | 0.56 | 8 | 0 | 7 | 6 | 0 | 4 | 0 | 0 |
| —$(CH_2)_5$— | | $CH_3$ | $CH_3$ | 11.2 | 8 | — | — | — | — | — | — | — |
| | | | | 4.48 | 7 | 0 | 0 | 0 | 0 | 0 | 0 | 0 |
| | | | | 1.12 | 2 | 0 | 0 | 0 | 0 | 0 | 0 | 0 |
| | | | | 0.56 | 0 | 0 | 0 | 0 | 0 | 0 | 0 | 0 |
| $CH_3$ | $CH(CH_3)_2$ | H | —$CH_2C{\equiv}CH$ | 11.2 | 9 | 0 | 8 | 9 | 3 | 8 | 8 | 8 |
| | | | | 4.48 | 9 | 8 | 8 | 9 | 8 | 8 | 8 | 8 |
| | | | | 1.12 | 7 | 2 | 8 | 9 | 2 | 7 | 7 | 8 |
| | | | | 0.56 | 6 | — | 8 | 8 | 0 | 7 | 6 | 5 |
| | | | | 0.28 | 5 | — | 7 | 8 | 0 | 3 | 2 | 0 |

| Structure | | | | Rate kg per | Plant Species | | | | | | | |
|---|---|---|---|---|---|---|---|---|---|---|---|---|
| $R_1$ | $R_2$ | $R_3$ | $R_4$ | Hectare | BA | CR | FO | WO | CN | CO | SY | RI |
| $CH_3$ | $CH(CH_3)_2$ | H | H | 11.2 | 7 | 6 | 7 | 4 | — | — | — | — |
| | | | | 4.48 | 2 | 2 | 2 | — | 2 | 7 | 7 | 1 |
| | | | | 1.12 | 1 | 1 | 1 | — | 2 | 2 | 3 | 0 |
| | | | | 0.56 | 0 | 0 | 0 | — | 0 | — | 1 | 0 |
| $CH_3$ | $CH(CH_3)_2$ | H | $CH_3$ | 11.2 | 0 | 0 | 0 | 0 | — | — | — | — |
| $CH_3$ | $CH(CH_3)_2$ | $CH_3$ | $CH_3$ | 11.2 | 0 | 1 | 5 | 1 | — | — | — | — |
| | | | | 4.48 | 2 | 0 | 1 | — | 4 | 8 | 8 | 2 |
| | | | | 1.12 | 0 | 0 | 0 | — | 4 | 8 | 7 | 0 |
| | | | | 0.56 | 0 | 0 | 0 | — | 0 | 4 | 0 | 0 |
| —$(CH_2)_5$— | | $CH_3$ | $CH_3$ | 11.2 | — | — | — | — | — | — | — | — |
| | | | | 4.48 | 0 | 0 | 0 | — | 0 | — | — | 0 |
| | | | | 1.12 | 0 | 0 | 0 | — | 0 | 0 | 0 | 0 |
| | | | | 0.56 | 0 | 0 | 0 | — | 0 | 0 | 0 | 0 |
| $CH_3$ | $CH(CH_3)_2$ | H | —$CH_2C{\equiv}CH$ | 11.2 | 7 | 6 | 8 | 5 | — | — | — | — |
| | | | | 4.48 | 9 | 9 | 9 | 8 | 8 | 8 | 8 | 9 |
| | | | | 1.12 | 8 | 9 | 9 | 6 | 7 | 7 | 5 | 7 |
| | | | | 0.56 | 6 | 7 | 9 | 4 | 1 | 3 | 5 | 1 |
| | | | | 0.28 | 5 | 5 | 5 | 0 | 1 | 1 | 2 | 0 |

I claim:

1. A method for the control of undesirable broadleaf weeds and grasses comprising, applying to the foliage of the undesirable broadleaf weeds and grasses or to soil containing seeds or other propagating organs thereof, a herbicidally effective amount of a compound having the structure:

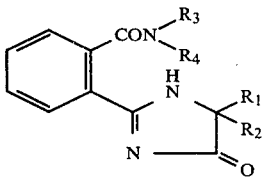

wherein $R_1$ is alkyl $C_1$–$C_4$; $R_2$ is alkyl $C_1$–$C_6$, cycloalkyl $C_3$–$C_6$, alkenyl $C_2$–$C_4$, phenyl, halophenyl or benzyl, and when $R_1$ and $R_2$ are taken together with the carbon to which they are attached they may form cycloalkyl $C_3$–$C_6$ optionally substituted with methyl; $R_3$ and $R_4$ each individually represent hydrogen, alkyl $C_1$–$C_4$, alkenyl $C_3$–$C_5$, alkynyl $C_3$–$C_5$, or benzyl; and the optical isomers thereof.

2. A method according to claim 1, wherein the undesirable plants are broadleaf weeds and control thereof is achieved by the application of the imidazolinyl benzamide to the foliage of the plants in an amount sufficient to provide from 0.28 kg to 11.2 kg per hectare of the imidazolinyl benzamide.

3. A method according to claim 1, for the preemergence control of dicotyledonous, cyperaceous and monocotyledonous plants comprising, applying to soil containing seeds or nutlets of the plants from about 0.28 kg to 11.2 kg per hectare of the imidazolinyl benzamide.

4. A method for the control of nutsedge comprising, applying to soil containing propagating organs of the nutsedge, from 0.28 kg. to 11.2 kg per hectare of the compound o-(5-isopropyl-5-methyl-4-oxo-2-imidazolin-2-yl)-N,N-dimethylbenzamide; o-(5-isopropyl-5-methyl-4-oxo-2-imidazolin-2-yl)-N-2-propynylbenzamide; o-(5-isopropyl-5-methyl-4-oxo-2-imidazolin-2-yl)-N- methylbenzamide; o-(5-isopropyl-5-methyl-4-oxo-2-imidazolin-2-yl)benzamide or N,N-dimethyl-o-(4-oxo-1,3-diazospiro[4,5]dec-2-en-2-yl)benzamide.

5. A method according to claim 4 wherein the compound is o-(5-isopropyl-5-methyl-4-oxo-2-imidazolin-2-yl)-N,N-dimethylbenzamide.

6. A method according to claim 4 wherein the compound is o-(5-isopropyl-5-methyl-4-oxo-2-imidazolin-2-yl)-N-2-propynylbenzamide.

7. A method according to claim 4 wherein the compound is o-(5-isopropyl-5-methyl-4-oxo-2-imidazolin-2-yl)-N-methylbenzamide.

8. A method according to claim 4 wherein the compound is o-(5-isopropyl-5-methyl-4-oxo-2-imidazolin-2-yl)-benzamide.

9. A method according to claim 4 wherein the compound is N,N-dimethyl-o-(4-oxo-1,3-diazospiro[4,5]dec-2-en-2-yl)benzamide.

* * * * *